United States Patent [19]

Beier et al.

[11] 4,305,126
[45] Dec. 8, 1981

[54] DENTAL TREATMENT INSTALLATION

[75] Inventors: Stefan Beier; Hermann Gmeinder, both of Biberach, Fed. Rep. of Germany

[73] Assignee: Kaltenbach & Voigt GmbH & Co., Biberach an der Riss, Fed. Rep. of Germany

[21] Appl. No.: 82,233

[22] Filed: Oct. 5, 1979

[30] Foreign Application Priority Data

Oct. 11, 1978 [DE] Fed. Rep. of Germany ....... 2844348

[51] Int. Cl.³ .................... G06F 15/20; A61C 19/02
[52] U.S. Cl. ..................... 364/413; 433/28; 433/101
[58] Field of Search ................... 364/413; 433/28, 101

[56] References Cited

U.S. PATENT DOCUMENTS 3,994,069 11/1976 Hohmann ..................... 433/28 X
4,106,198 8/1978 Childress ...................... 433/101 X
4,180,812 12/1979 Kaltenbach et al. ............. 433/28 X

FOREIGN PATENT DOCUMENTS 2434094 1/1976 Fed. Rep. of Germany .
2524056 12/1976 Fed. Rep. of Germany .

Primary Examiner—Felix D. Gruber
Attorney, Agent, or Firm—McAulay, Fields, Fisher, Goldstein & Nissen

[57] ABSTRACT

A dental treatment installation comprises a plurality of dental treatment instruments, a plurality of tools having different operating parameters and replaceably mountable in the instruments, and a main control device arranged to be supplied with the operating parameters of a selected instrument and optionally with further operating parameters, and to compute therefrom the operating point for the drive of the selected instrument and also the working data of the selected tool. The main control device includes stores which store the operating parameters of the tools under corresponding tool addresses or operating data addresses for the automatic control of the combined tool and instrument operation. A tool receiving station has receiving locations in which the tools are replaceably mounted and means is provided for transmitting automatically from said station to said main control device the tool address specific to a particular tool upon extraction of the latter from its receiving location.

18 Claims, 8 Drawing Figures

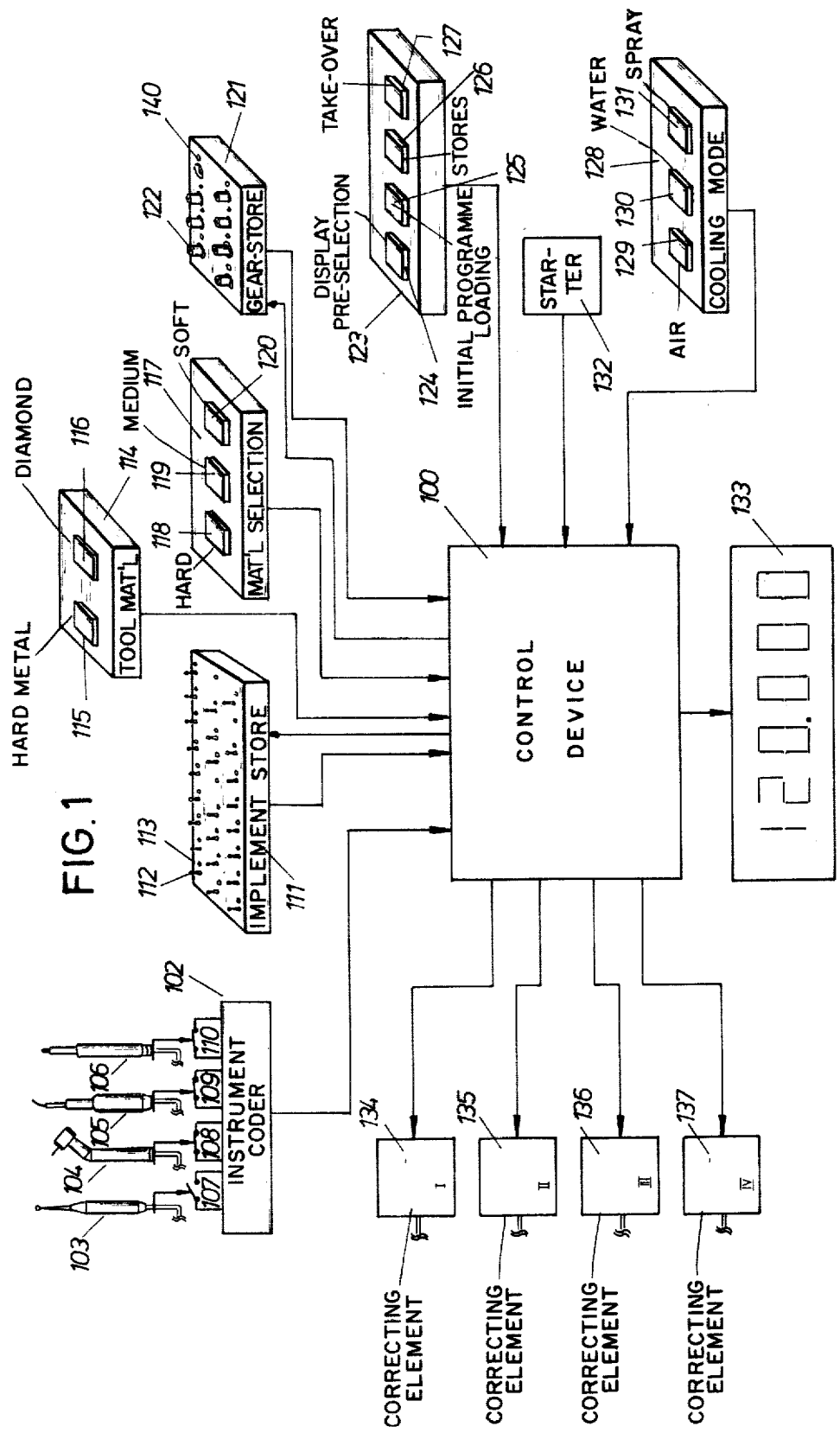

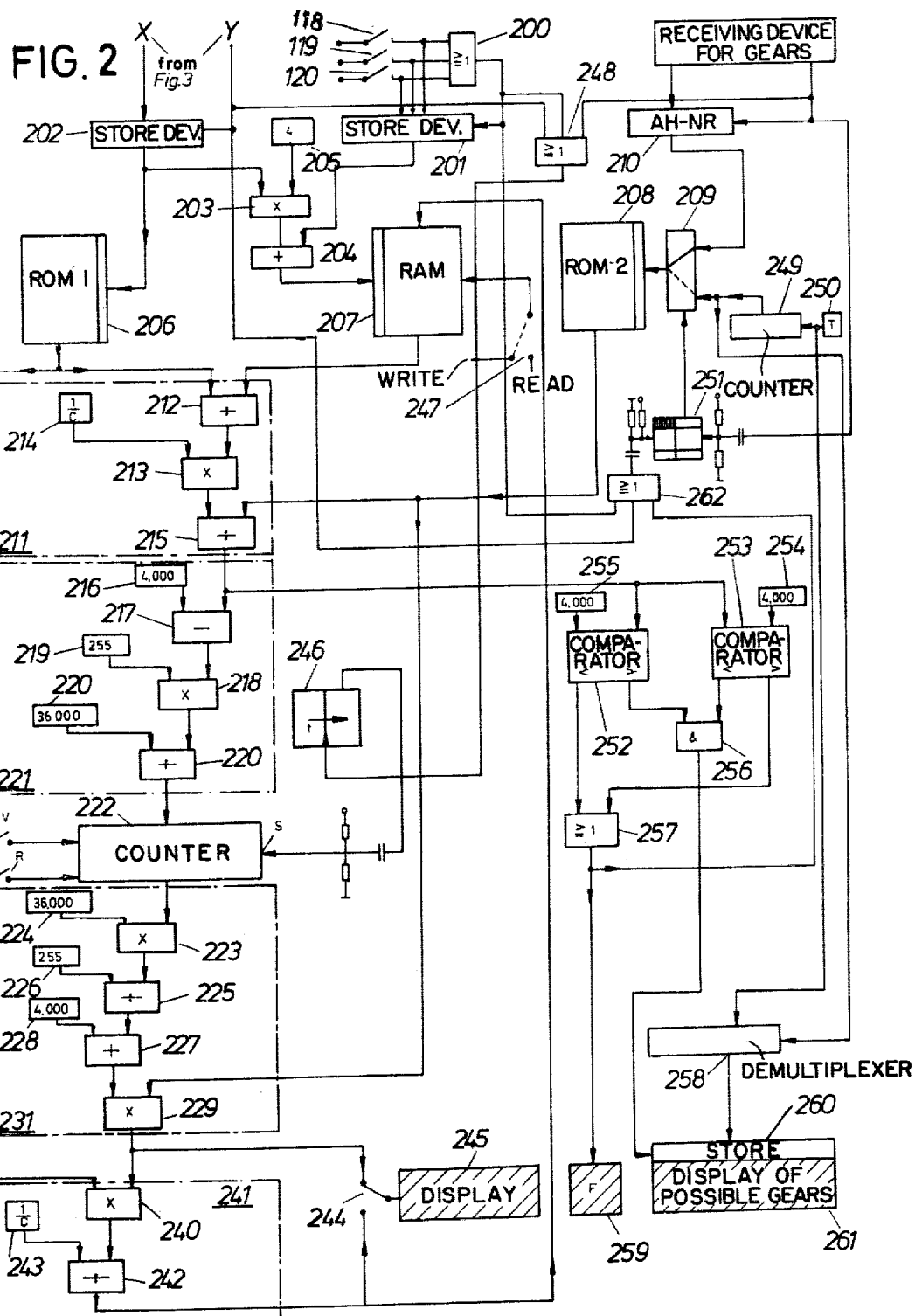

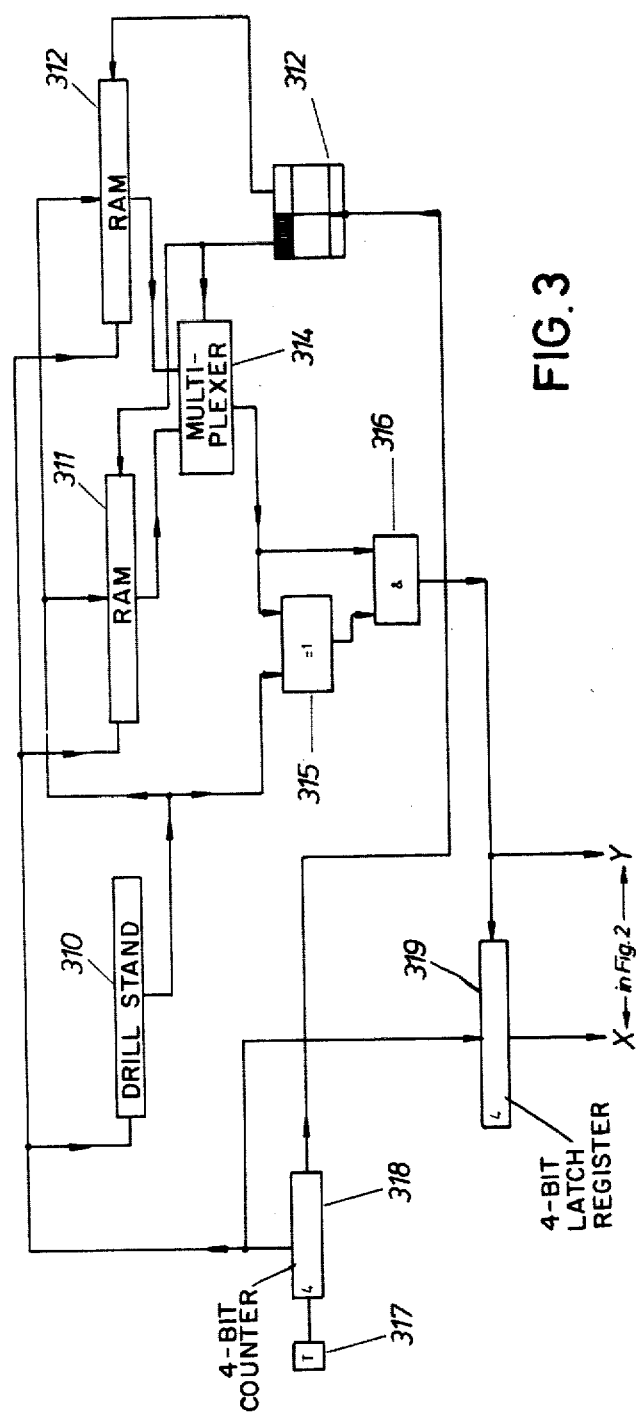

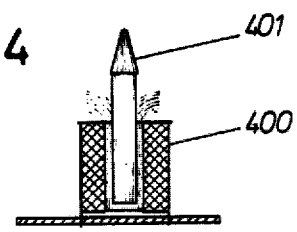
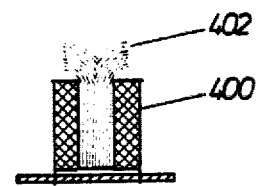
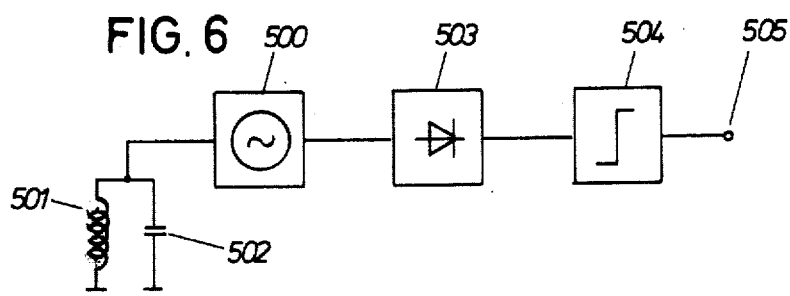
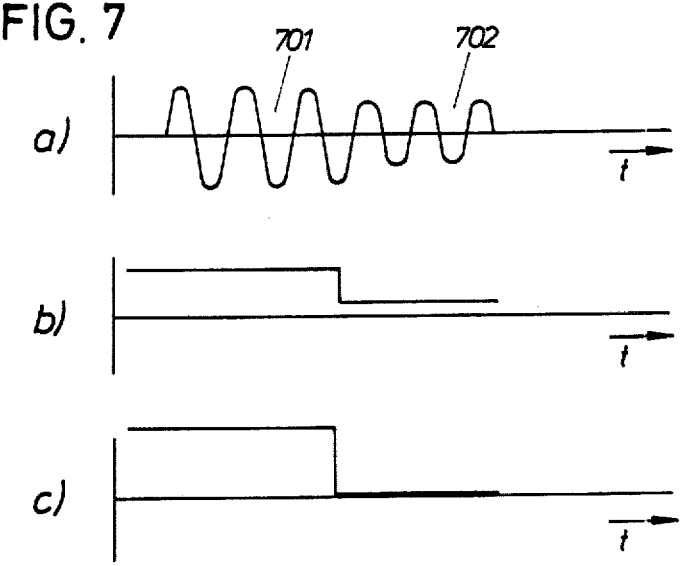

DENTAL TREATMENT INSTALLATION

BACKGROUND OF THE INVENTION

This invention relates to a dental treatment installation having one or more dental treatment instruments adapted to be actuated with replaceable or interchangeable dental tools having varying operational parameters, and a main control device to which the operating parameters of the particular treatment instrument selected and also if appropriate further operating parameters are fed, and which thereupon computes the operating point for the drive of the particular selected treatment instrument and also the working data of the particular selected tool.

DESCRIPTION OF THE PRIOR ART

There has already been proposed a dental treatment installation (see U.S. Pat. No. 4,180,812 which corresponds to German Application No. P 27 15 798.8), wherein there is provided at least one treatment instrument, for example a drilling machine, and wherein in a control data store predetermined control data fixed values, for example such as for predetermined speeds of the drilling machine, are stored and are adapted to be selectively called-out. Furthermore, in the case of this treatment installation a display device is provided. With the control data store, there is coupled a control element, constituting the main or central control device mentioned at the outset, for the treatment instrument. With the aid of this control element, the control data, starting from the fixed value called-off in each particular instance are variable. The appropriate control data store is adapted to be set by the control element or the central control device with instantaneous values of the control data as fixed values to be stored-in. The aforementioned display device is suitable for displaying variable values. Between the control element and the display device, there is connected a data converter converting the instantaneous values of the control data into corresponding operational data instantaneous values to be displayed. For supplying a display, there are employed or made ready, in all, three informations. The first information is derived from the employment of the particular treatment instrument. This information determines the absolute working zone of the treatment instrument employed in each particular instance. Thus, for example, an electric motor of a treatment instrument just at that instant to be employed may have an r.p.m between 4000 and 40,000 r.p.m. The second information relates to the working point within the afore-mentioned working range. This working range can be subdivided into a plurality of steps, for example 256 steps. The third information, finally, takes into account the transmission ratio of the gearing member employed in each particular instance and which is to be provided between the particular just-employed treatment instrument and the tool or implement to be driven thereby. Whereas the first two informations can be directly ascertained due to the central control device, the third information must be introduced manually into the central control device. From the thus-prepared three informations, then, the speed or the actual working range of the particular treatment instrument employed are ascertained and displayed.

Although the above-discussed dental treatment installation is to a considerable extent satisfactory, nevertheless sometimes introduction of the second and third information causes difficulty. In order to prepare the appropriate information, it is in fact necessary to ascertain the working ranges of the particular implement or gearing member employed and then to introduce corresponding data manually into the central control device. Therewith, however, there are connected uncertainties resulting for example due to the fact that, quite simply, data infeed takes place in faulty manner. Additionally, an undesirable time outlay is connected with this data infeed. Since the appropriate data are conventionally not available directly readable onto the implements or gearing members, but on the contrary are shown coded by coloured rings, it is furthermore necessary to possess appropriate knowledge in order to be able to feed the appropriate data into the central control device.

The information is based on the problem of how to indicate a mode whereby, in the case of a dental treatment location of the type mentioned at the outset, in relatively simple manner, all required data can be set ready for selection of the devices characterised thereby in the available central control device.

SUMMARY OF THE INVENTION

The above-indicated problem is solved in a dental treatment installation of the type mentioned at the outset, according to the invention in that the central control device comprises stores in which the operating parameters of the implements are stored-away under corresponding implement addresses or operating data addresses, and in that the implements are arranged at the receiving locations of an implement receiving system which, on extraction of an implement, supplies the implement address specific for this implement to the central control device. Therefrom, there is achieved the advantage that, due to the selection of an implement which is to be employed in connection with a treatment instrument still to be selected, already for the central control device there are prepared the necessary informations in order to ascertain and where appropriate to display the data necessary for the operation.

In a dental treatment installation, wherein between the drive device of at least one treatment instrument and the implement to be employed together with the appropriate treatment instrument, there are adapted to be inserted gearing members having varying transmission ratios, the mode of procedure adopted is expediently such that the central control device comprises a further store in which the operating parameters of the gearing members are stored under associated gearing addresses. A gearing display is provided which is connected with the central control device, and which displays one or more gearing members ascertained at the central control device whilst taking into consideration the operating parameters of the particular implement selected and also further fed-in operating parameters, such as for example the hardness of the material to be processed or the manner of cooling, which said gearing members are necessary and provided for the carrying into effect of the working data computed by the central control device of the particular selected implement. Thereby, it is ensured in advantageous manner that also the operating parameter of the particular selected gearing member is automatically available for the central control device, so that these data are then available for ascertaining where appropriate display of the working data of the implement employed in each particular instance.

Expediently, the gearing members are arranged at receiving locations of a receiving device transmitting to the central control device, on extracting a gearing member, the specific gearing address for this gearing member, and furthermore there is provided a fault or error display device supplying a fault or error display in cases wherein there is extracted out of the receiving device a gearing member which is not displayed by the gearing display device as extractable gearing member. Thereby, it is assured, in a especially simple manner, that faulty extraction of a gearing member which is not correct for utilisation can already be noted prior to effecting a treatment process.

The fault display device and a display device provided for displaying the particular operating parameter are expediently constituted by a single display device. This is especially advantageous from the aspect of the circuitry outlay required.

Expediently, the receiving locations for the implements and/or gearing elements are interrogated cyclically successively, in each particular instance, with regard to the presence of an implement or gearing member and, on ascertaining a deviation between the implementing conditions of one and the same receiving location, during two successive interrogations there is obtained a display signal on the occurrence of which the address designating the appropriate receiving location can be utilised as the address designating an employed implement or gearing member. Thereby, there results the advantage that in an especially simple manner extraction of an implement or gearing member from its receiving location can be recognised and in that furthermore the continuous non-presence of implements or gearing members is not evaluated in or at corresponding receiving locations as extraction. Thereby, furthermore, the mode of procedure may be such that depositing of an implement or gearing member at a receiving location does not result in transmission of a display signal.

Expediently, the gearing members necessary on detecting a treatment instrument, an implement and where appropriate the nature of cooling provided are indicated adjacent their receiving locations by separate display elements. Thereby, there is achieved the advantage of especially reliable display of the particular gearing members which are appropriate for utilisation.

The display elements are preferably photodiodes or incandescent bulbs.

Preferably, there is associated with each receiving location a coil connected with an oscillator the supplied oscillation signals which have values differing from each other in their amplitude due to the presence or non-presence of an implement or gearing member at its associated receiving location, occurrence of a deviation of such a value from a reference value being employed for supplying a display signal. This provides for a relatively reliable ascertainment of when an implement or gearing member is extracted from its associated receiving location, without it being for this purpose necessary to employ special materials for the appropriate gearing members or implements. On the contrary, it suffices that due to the material of the particular gearing member or implement there is produced a variation of the stray field generated by the particular coil, with which there is connected a corresponding amplitude variation in the oscillation signals.

Expediently, each of the said coils is designed as an air-core coil. Thereby, especially simple coil assembly becomes possible.

The coils of all the receiving locations are expediently connected cyclically in succession with the oscillator. Thereby, there is achieved the advantage that it is possible to "make do" with only one oscillator, this is significant from the circuit-technical outlay aspect.

Signals corresponding to the oscillation signals obtained by interrogating in each particular instance one and the same receiving location during two successive interrogation cycles are expediently stored in two separate stores and the signals associated in each particular instance with one and the same coil of the two stores are compared with each other while supplying a display signal. With the use of the aforementioned signals, use is made of the so-called last-look principal.

For successive connection of the coils of all the receiving locations with the oscillator, the mode of procedure is expediently such that an address generator transmits addresses designating all of the receiving locations and from which there may be derived, by means of a decoder, control signals for the closure of switches via which the coils are connected with the oscillator. Thereby, there is achieved the advantage of an especially slight circuit-technical outlay for effective connection of the coils with the single oscillator provided.

A further expedient design of the invention results from the fact that, due to extraction of an implement or a gearing member from its associated receiving location, a display element disposed at this receiving location is adapted to be effectively controlled to supply a special display signal, in particular a blinking or winking signal. Thereby, there is achieved the advantage that in an especially simple manner it becomes possible to mark that particular or individual receiving location from which an implement or gearing member has been extracted.

The operating data ascertained in each particular instance in the central control device are expediently retained in a counter the particular counting position of which is furthermore variable by separate triggering. Thereby, there is achieved the result that the per se automatically detected operating data are also variable manually and can therefore be adapted to special conditions which are not taken into account by the data contained in the afore-mentioned stores.

Expediently, the counter position of the counter or an operating data information derived therefrom is adapted to be stored into the one store associated with the central control device under a just-available operating data address. Thereby, there is achieved the advantage that, in the event of renewed appearance of the same operating data address, setting ready of these informations stored in the said one store once again takes place. Thus, the appropriate one store is designed as a read-write store.

In order to have immediately available (on putting the installation into effect) appropriate operating data, expediently in the afore-mentioned store there are separately storable data associated with an initial programming program and corresponding to experience values on employing the operating instruments and implements. The said original programming program data can be called-off from a fixed value store in response to separate triggering.

Expediently, there are adapted to be displayed with reference to extraction of a second treatment instrument, after extraction has already been effected of a first treatment instrument, out of the instrument receiving device provided for receiving the treatment instrument, due to transmission of a separate actuating signal, the operating data decisive for the said second treatment instrument. Therefrom, there is achieved the advantage that during operation with the afore-mentioned first treatment instrument there can already be prepared a second treatment instrument for a treatment and the display necessary for that purpose is already available after extraction of the second and subsequent to the presence of the separate actuating signal.

One embodiment of the invention will now be described in detail, by way of example only, with reference to the accompanying drawings in which:

BRIEF DESCRIPTION OF THE DRAWINGS

FIG. 1 is a diagrammatic illustration of a dental treatment installation according to the invention;

FIG. 2 is a block circuit diagram of a main control device of the installation shown in FIG. 1;

FIG. 3 is a detailed block circuit diagram of a part of the control device shown in FIG. 1 for ascertaining the address of a tool to be employed;

FIG. 4 shows, diagrammatically in a sectional elevation, a tool received in a receiving location of a receiving device;

FIG. 5 shows the receiving location shown in FIG. 4, without a tool;

FIG. 6 is a block circuit diagram of a circuit arrangement which may be provided per tool-receiving location;

FIG. 7 is a signal-time diagram illustrating the travel of signals to various points of the circuit arrangement shown in FIG. 6.

DESCRIPTION OF THE PREFERRED EMBODIMENTS

Figure 8:
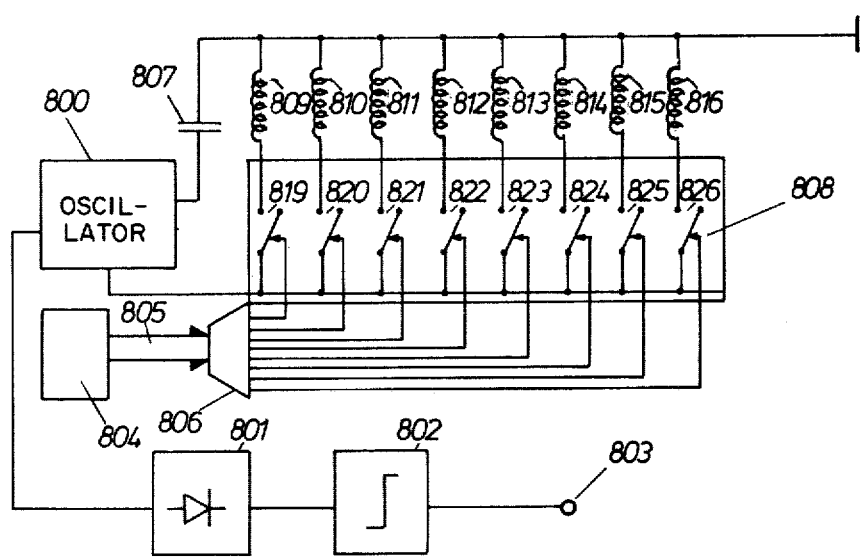
FIG. 8 is a block circuit diagram of a circuit arrangement which may be provided for a plurality of tool-receiving locations.

The dental treatment installation shown in FIG. 1 has, as essential elements, a control device 100 which may be constituted as central control device by a computer and in particular by a micro-computer which is provided with at least one microprocessor. The control device 100 has a series of inputs and a series of outputs. Connected to one of the inputs of the control device to the output of an instrument coder 102. The said instrument coder 102 cooperates with and is associated with dental treatment instruments 103, 104, 105 and 106 which, subsequent to their particular extraction out of an instrument receiving device (not shown), are in each particular instance able to close or to open an associated switch of the switches 107, 108, 109 or 110 shown in FIG. 1. Of these treatment instruments, the treatment instrument 103 may for example be a turbine drill machine; the treatment instrument 104 may be a standard drilling machine; the treatment instrument 105 may be a tartar-removing instrument; the treatment instrument 106 may be a UV-instrument. Of these treatment instruments, at least the standard drilling machine 104 is to be employed in combination with gearing members and tools or implements such as will become apparent in greater detail hereinbelow. In the present case, the turbine drilling machine 103 may also be operated with corresponding gearing members and implements. With extraction of one of these treatment instruments out of the associated receiving device, the associated switch, such as the switch 107, may be opened, whereupon the instrument coder 102 transmits to the control device 100 an address designating the appropriate treatment instrument.

The control device 100 is connected by a further input to the output of an implement store 111. The said implement store 111 has a plurality of receiving locations for workpieces or tools 112. Associated with each such receiving location is a display element 113 and what is concerned here may be a photodiode LED or an incandescent lamp. At this point it should also be pointed out that it is not necessary that all the receiving locations should be occupied by implements such as the implement 112, in order to guarantee functionality of the implement store 111. There will be further reference to this hereinbelow.

Connected with yet a further input of the control device 100 is the output of a selector 114; what is concerned here may be an implement-material store having two push buttons 115 and 116. The push button (or key) 115 is to be actuated if an implement having a hard-metal cutting head is selected to be employed. The push button (or key) 116 is to be actuated if an implement having a diamond instrument head is selected to be employed. The information is transmitted to the control device 100 and from the control device 100 to emplement store 101 and gear-store 121.

With a still further input there is connected to the control device the output of a selecting device 117 having material selecting push buttons 118, 119 and 120. Of the said push buttons, the push button 118 is actuated if the material to be processed is hard. On the other hand, the push button 119 is actuated if the material to be processed has an average degree of hardness. The push button 120 is, finally, actuated on processing soft material.

With a still further input, the control device 100 is connected to the output of a gearing store 121 which may have a series of gearing members 122 at corresponding receiving locations. Adjacent each receiving location there may be a display device 140, for example in the form of a photodiode or incandescent lamp which is responsive to information from the control device 100. There will be further reference thereto, in greater detail, hereinbelow.

The control device 100 is furthermore connected by a further input to the output of a push button arrangement 123 which, in the present case, may comprise four push buttons 124, 125, 126 and 127. Of these push buttons, the push button 124 may be employed for so-called display pre-selection, so as for example to monitor the number or address of a gearing member 122 extracted from the gearing store 121 on a display device 133 connected to an output of the control device 100. The push button 125 is operated when a store associated with the control device 100 is subjected to so-called initial program loading. As will be further ascertainable hereinbelow, during such initial program loading there are stored into the said store operating data corresponding to experience values of the individual treatment instruments and implements. The push button 126 is actuated if there are to be retained or stored operating data displayed by the display device 133 and which deviate from the corresponding initial program loading data. The push button 127 is, finally, actuated when, subsequent to extraction of a treatment instrument out of the associated treatment receiving device, also a second treatment instrument is to be extracted and the data thereof are to a certain extent to be taken-over by the display device 133.

The control device 100 has, in addition to the inputs hitherto considered, also two further inputs. With one of these inputs the control device 100 is connected to the output of a starter 132 which may be designed in the same manner as the starter in the case of the above-mentioned, already proposed dental treatment installation. Consequently, the starter 132 may not only control cutting-in and cutting-out of the particular treatment instrument, but additionally control also the drive direction of the implement employed in each particular instance.

With the other of the two last-mentioned inputs, the control device 100 is connected to the output of a further push button field 128 which in the present case may have three push buttons 129, 130 and 131. These three push buttons are actuated to correspond to the particular cooling mode employed. The push button 29 is actuated in the case of cooling by air; push button 130 is actuated on cooling by water, and push button 131 is actuated on cooling by spray, i.e. in the case of a mixture of air and water.

In addition to the output connected with the display device 133, the control device 100 has also further outputs whereof in the present case only four outputs are indicated. With one of these outputs, there is connected a drive element I designated 134. With the second of the afore-mentioned outputs, there is connected a drive element II designated 135, with the third of the appropriate outputs there is connected a drive element III designated 136, and with the last of these four outputs there is connected a drive element IV designated 137. These drive elements are individually associated with the treatment instruments 103 to 106. Due to supplying of appropriate control data from the control device to these drive elements 134 to 137, the associated treatment instruments are operated with the operational values ascertained in each particular instance.

In connection with the display instrument 133 indicated in FIG. 1, it should also be pointed out that what is concerned here may be a display instrument comprising six numerical elements, each of the numerical elements of which may be a 7-segment numerical (or digit element).

Hereinbelow, there is discussed in detail the embodiment of the control device 100 shown in FIG. 2. In this connection, it should be pointed out that in FIG. 2 there is illustrated merely the essential structure of this control device 100. Thus, the processing of the addresses supplied by the instrument coder 102 according to FIG. 1 is not shown in detail in FIG. 2. On the contrary, in FIG. 2 there are shown only those circuit elements which, in combination with extraction of an implement out of the implement store 111 and in combination with actuation of one of the push buttons of push button fields 114, 117 and extraction of a gearing member out of the gearing store 121, play a significant part. In this connection, it is presumed that corresponding treatment instruments have been extracted from the instrument extraction device provided. Accordingly, assumption of corresponding information by the store device 202 or supplying of such information from the said store device 202 may be a function of the selection of the treatment instrument.

In the store device 202 there is the address of the particular implement precisely extracted from the implement store 111 according to FIG. 1. This address results on the one hand in the triggering of a fixed value store ROM1 designated 206. In the said store 206, at addressed store locations, there are contained operating data of the individual implements which are available in the implement store 111. With regard to these operating data, in the present case what is concerned may, by way of example, be the diameter in mm of the particular implement or drill.

This implement data information is delivered from the store 206 to in each particular instance one input of two processing devices 211 and 241.

In the processing device 211, the implement-data information transmitted from the store 206 are supplied to a dividing device 212 to which additionally operating data are fed from the output of a read-write store RAM designated 207. These operating data are stored in individual storing locations which can be triggered from the output of an adding device 204. The said adding or addition device 204 is connected by an input to the output of a multiplication device 203 and by a further input to the output of a store device 201 which supplies an information with reference to the particular implement material and/or material to be processed and is induced at the input side, due to actuation of a corresponding number of push buttons, to supply such information.

This means that the store device 201 satisfies, to some extent, a coding function. Referring to FIG. 2, there are there shown merely the material-selection push buttons 118, 119 and 120 already indicated in FIG. 1. However, there may also be provided the push buttons 115 and 116 shown in FIG. 1.

The afore-mentioned multiplication device 203 is connected with one of its inputs to the output of the store device 202. With its other input, the multiplying device 203 is connected to the output of a fixed value datum source 205 which in the present case may supply a fixed value of, by way of example, 4. With the said fixed value 4 there is multiplied the implement address supplied in each particular instance by the store device 202, and to the thus formed product there is added the number or address of the particular actuated material push button so as finally to form an unequivocal address for triggering a desired storage location at the store 207. In this storage location there is then stored as operating data information a display indicating at which velocity or r.p.m. the just-selected implement is to be actuated. This information is fed to the second input of the already mentioned dividing device 212 of the processing device 211.

The just-mentioned dividing device 212 is connected at the output side with an input of a multiplying device 213 connected with a further input to a fixed value datum source 214. The said fixed value datum source supplies a fixed value of $1/C$, in which connection C satisfies the equation $C = \pi/1000.60$. The output signal supplied from the output of the multiplication device 213 indicates the motor desired r.p.m. resulting from employment of the selected implement or drill and the operating data thereof stored in the store 207. This data information is then divided in the dividing device 215 by a value indicating the transmission factor of the gearing member actually employed, and which is employed between the treatment instrument and the selected implement. The transmission factor variable is supplied from the output of a desired value store ROM2 designated 208, which contains at individual store locations so-called transmission values associated with the gearing members contained in the gearing store 121 according to FIG. 1. The said store 208 is addressable via a lock-circuit controller 209 connected with one of its input sides to the output of a store device 210 serving for taking up the address or number of the particular gearing member to be employed. This is designated AH-NR in the receiving device (FIG. 2).

In response to supplying of the transmission data information concerned from the store 208, the division device 215 transmits at the output side information representing the actual motor desired r.p.m. to a processing device 221. This magnitude satisfies the relationship $n=(V/d \cdot C) \cdot 1/u$, wherein V signifies the cutting velocity variable in m/s, supplied by the store 207, d signifying the diameter of the implement employed in mm and C having the above-indicated value, whereas u signifies the transmission factor of the gearing member and is supplied from the store 208.

The output variable supplied from the processing device 211 is fed in the processing device 221 to a subtraction device 217 to which additionally a fixed value of 4000 is fed from a fixed value datum source 216. The output-different signal supplied from the subtracting device 217 is, with the aid of a multiplication device 218, multiplied by a fixed value supplied from a fixed value device 219, and the product thus formed is fed to one of the inputs of a division device 220 which receives fed to it at a further input a fixed value of 36,000 from a further fixed value device 220. From the output of the dividing device 220 and therewith from the output of the processing device 221, there is obtained a data information representing a binary correcting variable Z and which is fed to a counter 222 which is a forward-backward counter having, in addition to a setting input S also two further inputs adapted to be subjected to special counting pulses by means of a V push button or an R push button, and making it possible to vary the counter position of the counter 222 in the forward direction (V) or in the rearward direction (R). Due to actuation of the push buttons V,R, it is therefore possible to modify the data information supplied by the processing device 221. This data information or correcting variable Z satisfies the relationship $$Z = (n - 4000)(255/36000)$$

wherein n has the significance indicated hereinabove.

The particular counter position of the counter 222 is fed to one of the inputs of a further processing device 231, i.e. in particular to one of the inputs of a multiplication device 223 connected with a further input to a fixed value datum source 224 supplying a fixed value of 36,000. The product supplied from the multiplication device 223 is fed to a dividing device 225 to which additionally a fixed value of 225 is fed from a fixed value datum source 226. The output signal of the dividing device 225 is fed to an addition device 227 to which additionally there is fed from a fixed value datum source 228 a fixed value of 4000. The result of the addition is fed to one of the inputs of a further multiplication device 229 to which are fed at a further input the transmission values or data of the store 208. From the output of the last viewed multiplication device 229 and therewith of the processing device 231, there is supplied a variable representing the velocity N of the implement employed. This variable satisfies the relationship $$N = [4000 + 36,000(Z/255)] \cdot u$$

The last-mentioned r.p.m. magnitude is on the one hand fed to the processing device 241 already mentioned hereinabove and on the other hand passes via change-over means 244 to a display device 245 representing the display device 133 indicated in FIG. 1. In the processing device 241, the r.p.m. magnitude is multiplied in a multiplication device 240 with the data supplied from the store 206, and the product thus formed is fed to a division device 242 which additionally receives a fixed value 1/C fed to it from a fixed value datum source 243. From the output of the processing device 241, there is supplied a variable representing the cutting velocity V of the implement employed. This variable V satisfies the relationship $$V = N \cdot d \cdot C$$

The dimension of this variable may be m/s. This cutting r.p.m. variable is, with an appropriate switch position of the change-over means 244 indicated by means of the display device 245. Furthermore, this cutting r.p.m. variable is adapted to be stored into the store 207 containing operating data, for which purpose the store push button 247 indicated in FIG. 2 is to be correspondingly actuated. Thereby, then, this cutting velocity variable representing the operating data for the implement just employed and the actuated material selection push button is stored under the operating data address just available in the store 207; the appropriate cutting velocity variable can, with renewed feed of the same operating data address, be once again prepared or set ready by the store 207.

As already mentioned hereinabove, the store 208 supplies, in response to appropriate triggering via the data switchpoint 209 at the output side, a transmission data information indicating the transmission factor of an employed gearing member. The data switchpoint 209 is correspondingly controlled from the output of a bistable rocker or sweep element 251. In its other switch-through position, the switchpoint circuit 209 connects the output of a counter 249 with the addressing input of the store 208. This counter 249 has master clock pulses fed to it from a pulse generator 250, so that it successively varies its counter position. Thereby, there are triggered all store locations of the store at which there are corresponding transmission-data informations. These data are employed in the processing device 211 for ascertaining the motor desired r.p.m. values which become significant in each particular instance on employing the associated gearing members. These data are fed to the one set of inputs of two comparators 252, 253 which compare these data with fixed values of 4000 or 40,000 supplied from fixed value datum sources 255 or 254. These two fixed values determine the permissible r.p.m. range. If the data supply falls below or exceeds the limits given by the two fixed values, then via an OR element 257, a faulty display signal is transmitted to a fault display device 259 which can form, with the display device 245, a common display device which may be the display device 133 shown in FIG. 1. In response to the occurrence of such a faulty display signal, the appropriate display device supplies the display "FAULT" or "WRONG" or "ERROR". If, on the other hand, the afore-mentioned data information is within the permissible r.p.m. range, then, via an AND element 256 this information is supplied to a store 260 and is stored under the determining address supplied via a demultiplexer 258, at the appropriate instant, from the counter 249. In this manner, one after the other all the addresses possible for the case of application considered are detected. These gearing members (also designated handpieces) are indicated by means of a display device 261. This display device may be photodiodes or incandescent lamps disposed at the individual receiving locations at which the gearing members are mounted. These display elements light up if their associated gearing member is considered to be a just-employed gearing member.

Supplementation with regard to the above-discussed mode of triggering the store 260, it should also be pointed out that there is written into the addressed storage locations thereof the bit information supplied from the output of the AND element 256.

The rocking or sweeping position of the bistable rocker or sweep element 251 is a function of the triggering of the said rocker or sweep element. With a setting input, the bistable sweep element 251 is connected to the output of an OR element 262. The said OR element 262 is connected with one of its inputs to the output of the OR element 257. With a further input, the OR element 262 is connected to the output of a further OR element 200 which, on actuation of one of the push buttons 118, 119, 120, supplies a corresponding binary signal. With a further input, the OR element 262 is connected to a line on which there appears a pulse if or when an implement is extracted out of its associated receiving device. Thus, thereby, with each extraction of an implement out of the associated receiving device and/or with each actuation of a push button determining the material selection, display of the gearing members concerned is guaranteed. The fault signalling signals supplied from the output of the OR element 257 have a corresponding effect on the setting input of the bistable sweep element 251.

With extraction of a gearing member out of the associated receiving device, there is fed to the reset input of the bistable sweep element 251 a reset signal on occurrence of which the switchpoint circuit 209 passes into its other switch-through position in which the output of the store device 210 is connected with the address input of the store 208. Then, in the receiving device 210 there is the address of the gearing member extracted out of the just-mentioned receiving device.

The above-mentioned counter 222 is connected, with its setting input S, at the output of a delay element constituted by a monostable rocker or sweep element 246. The said monostable sweep element 246 is connected at the input side to the output of an OR element 248. Thereby, the monostable sweep element 246 is in each particular instance caused to transmit an output pulse if or when an implement has been extracted out of the associated receiving device and/or a gearing member has been extracted out of the associated receiving device and/or one of the material selecting push buttons has been actuated. The setting pulse thereupon transmitted from the monostable sweep element 246 produces the result that the counter 222 then is able to take-over the binary correcting variable supplied to it from the processing device 221. With this arrangement, the delaying time introduced by the monostable sweep element 246 takes into account the processing time of the circuit or switching elements which bring about ascertainment and delivery of the just-mentioned binary correcting variable.

There will now be detailed discussion of the block circuit diagram shown in FIG. 3. This block circuit diagram indicates an arrangement able to detect valid extraction of an implement, such as a drill, from its associated receiving location in a receiving device. Referring to FIG. 3, a 4-bit counter 318 triggered by a pulse transmitter 317 supplies successive addresses for the addressing of two read-write stores 311 and 312 and also of a drill stand 310 representing an implement receiving means. In the said drill stand 310, the individual receiving locations of the implements are triggered in correspondingly addressed fashion, the particular result being fed in the form of a bit to the writing inputs of the two stores 311 and 312 and also to one of the inputs of an exclusive-OR element 315. The said exclusive-OR element is connected on the output side with an input of an AND element 316. The other input of the said AND element 316 is connected with the other input of the exclusive-OR element 315 at the output of a multiplexer 314 which, depending on its setting, connects either the output of the store 311 or the output of the store 312 to the just-mentioned inputs of the two linking elements 315 and 316. The adjustment of a multiplexer 314 is effected by a bistable sweep element 312 connected with its two outputs additionally with control inputs of the two stores 311 and 312. Depending on triggering, in each particular instance one of these two stores 311 and 312 is in writing operation, whereas the other store is in reading operation. The store in reading operation is then connected with its output via the multiplexer 314 with the just-mentioned inputs of the two linking elements 315 and 316.

The bistable sweep element 312 is connected with its pulse input to a transmission output of the counter 318. This means that the bistable sweep element 312 changes over whenever the counter 318 has travelled through all the counter positions.

Connected at the output of the AND element 316 is a 4-bit-latch register 319 having an enable input. This register 319 represents a take-over register which, in response to a corresponding triggering of the AND element 316, takes-over the address transmitted at the instants in time concerned from the 4-bit counter 318. This address is then transmitted by the register 319 at the switching instant designated x in FIG. 2. The output signal of the AND element 316 is transmitted at the switching point y indicated in FIG. 2. Due to the switching or circuit arrangement shown in FIG. 3, it is therefore possible to recognise extraction of an implement or drill out of the receiving device or the drill stand 310 and to display this by delivery of a binary "1" signal from the output of the AND element 316. Simultaneously with transmission of such a binary signal, there is then available the address of the appropriate receiving location from which the associated implement can be extracted. The circuit arrangement considered can (and this should be mentioned in supplementary fashion here) be employed in principle also for ascertaining the extraction of gearing members out of the gearing store.

In order then to be able to recognise the extraction of an implement or a gearing member from the associated receiving location, it will be possible to associate with each receiving location a contact which is closed for example on extracting an associated workpiece or gearing member. However, according to the invention the arrangement is that, at least for ascertaining the extraction of implements from their receiving locations, there is provided a coil arrangement as indicated in FIGS. 4 and 5. In this connection, FIG. 4 shows an air-core coil 400 having an implement 401 received therein. FIG. 5 shows the air-core coil 400 without implement. Viewing of FIGS. 4 and 5 will show that, in the event of an implement being absent from the coil 400, this coil will have a stronger stray field 402.

Each of these coils can be included, in the manner shown in FIG. 6, in an evaluation device. The said evaluation device comprises on the one hand an oscillator 500 the oscillation frequency of which is determined by the inductance 501 of a coil and the capacity of a capacitor 502. The oscillation amplitude of the oscillator 500 is a function of the magnitude of the stray field of the appropriate coil. Connected to the output of the oscillator 500 there may be a rectifier circuit 503 connected sequentially of which is an amplitude swell-value circuit 504 (for example a comparator), which is able to supply output signals at an output 505.

In order to make more readily comprehensible the mode of operation of the circuit arrangement indicated in FIG. 6, reference is made to FIG. 7. In line (a), FIG. 7 shows the travel of the oscillation signals transmitted from the oscillator 500 according to FIG. 6. With this arrangement, it is indicated by the signal configuration 701 that an implement such as the implement 401 has been extracted from its associated receiving location, i.e. out of the coil 400. The signal configuration 702 illustrates the oscillation amplitude of the oscillator 500 for the case that an implement such as the implement 401 is in its associated coil 400. Out of these oscillation signals indicated in FIG. 7a, the rectifier circuit 503 generates the signal shown in FIG. 7b which then leads to supplying of the signal shown in FIG. 7c from the output 505 of the circuit arrangement according to FIG. 6. Therewith, it should be apparent that unequivocal ascertainment of the presence or non-presence of an implement at its associated receiving location is possible. The same switching principle can naturally also be applied for ascertaining the presence of gearing members at corresponding receiving locations.

Referring to FIG. 8, there is then indicated a modification of the circuit principle shown in FIG. 6. Referring to FIG. 8, the coils 809 to 816 associated with the individual receiving locations are not each connected with an oscillator of their own, but they are on the contrary associated with a single oscillator 800. With this arrangement, the oscillation frequency of the oscillator 800 is, as in the case of the circuit arrangement shown in FIG. 6, determined by the capacity of a capacitor 807 and by the inductance of the coil 809 to 816 employed in each particular instance. These coils 809 to 816 are connected with one set of their ends jointly with the one connection of a capacitor 807 to earth. At their other ends, the coils 809 to 816 are connected to switches 819 to 826 associated individually with them of a switch field 808, which makes it possible, via th aforementioned switches 819 to 826, to connect the individual coils 809 to 816 individually with the oscillator 800. In order to establish this connection, actuating signals are fed to the actuation inputs of the afore-mentioned switches 819 to 826 from the output of a decoder 806. The decoder 806 is connected via an address line to the output of an address generator 804. The said address generator 804 is able to supply, following cyclically one upon the other, such addresses that one after the other each of the switches 819 to 826 is closed for a short instant. During the closure duration of the particular switch, then the coil connected with this switch (such as the coil 809) is drawn into the oscillation circuit of the oscillator 800.

As in the case of the circuit arrangement shown in FIG. 6, also in the case of the circuit arrangement shown in FIG. 8, a rectifier circuit is sequentially connected to the output of the oscillator 800 and the rectifier circuit 801 has sequentially to it an evaluation circuit, for example a comparator 802, for supplying corresponding output signals at an output 803. In principle, the circuit arrangement shown in FIG. 8 operates as discussed with reference to FIG. 7.

Finally, consideration should be given also to some features of the present invention which have not been precisely referred to in discussing FIGS. 2 to 8. Thus, in the implement store 111 indicated in FIG. 1 and also in the gearing store 121 indicated in FIG. 1, it is not necessary that all receiving locations should be occupied by implements or gearing members, so as nevertheless to make it possible to recognise removal of an implement or gearing member from its associated receiving location. This is possible just by reason of employment of the last-look principle discussed with reference to FIG. 3. With this arrangement, the display instrument associated with the particular receiving location may, after effected extraction of the associated implement or gearing member, be induced to transmit a display signal, in particular a blinking signal, so that there is available a display as to where the implement or gearing member just extracted is to be redeposited, if it is no longer required. In this connection, it should also be pointed out that according to FIG. 1, there are individually associated separate display instruments only with the individual implement receiving locations, but that additionally also a gearing display device could be provided.

In order to be able to put into operation the treatment installation shown in FIG. 1, it is necessary that the store 207 indicated in FIG. 2 should have corresponding operating data. The said operating data can now, with putting into operation of the treatment installation, be introduced into the said store 207 from a so-called initial program loading program, as already indicated hereinabove. However, during operation (as discussed in reference to FIG. 2) such data may be varied in the store 207, which is preferably operated from a buffer battery, so as not to immediately lose the store content thereof in the event of mains or line voltage failure.

With reference to the block circuit diagram shown in FIG. 2, it should also be pointed out that the store devices 201, 202 and 210 there shown can be constituted by store registers. Furthermore, with reference to FIG. 2 it should also be pointed out that the arrangement shown there operates in the same manner if, after extraction of a first treatment instrument out of the provided instrument receiving device, also a second treatment instrument is extracted and the push button 127 of the push button field 123 indicated in FIG. 1 is actuated.

Finally, it should be pointed out that in deviation from the relationships discussed with reference to FIG. 8, it is also possible to proceed in such manner that in each particular instance such a circuit arrangement is provided for the implement store 111 and for the gearing store 121 according to FIG. 1.

We claim:
1. A dental treatment installation comprising:
   at least one selected dental treatment instrument;
   a plurality of tools having different operating parameters and replaceably mountable in said instrument;
   a main control device arranged to be supplied with the operating parameters of a selected instrument and optionally with further operating parameters, and to compute therefrom the operating point for the drive of the at least one selected instrument and also the working data of the selected tool;

stores provided in the main control device for storing the operating parameters of said tools under corresponding tool addresses and operating data addresses;

a tool receiving station having receiving locations in which the tools are replaceably mounted; and means for transmitting from said station to said main control device the tool address specific to a particular tool upon extraction of the later from its receiving location and automatically making available the operating parameters of the respectively employed tool required for computing the operating point, and upon extraction of said particular tool from said tool receiving station, a specific address for said tool causes the connection of the store for said operating parameters for said particular tool indicated under the address for said tool store in said stores.

2. A dental treatment installation according to claim 1, including interchangeable gearing members having different gear ratios and insertable selectively between the drive device of said instrument and the tool to be employed therewith, and a gearing-display device, in which:

said main control device comprises a further store in which the operating parameters of gear members are stored under corresponding gear addresses; and said gear-display device is connected to said main control device for displaying one or more gear members ascertained by the main control device taking into consideration the operating parameters, such as, for example, the hardness of the material to be processed or the mode of cooling, which said gear members are necessary and available for realization of the working data computed by the main control device of the tool selected in each particular instance.

3. A dental treatment installation according to claim 2, including a gearing store having receiving locations for said gear members and arranged to transmit to the main control device, upon extraction of a selected gear member from the receiving device, the address specific for this particular gear member, and an error or fault display device arranged to supply an error fault display in cases wherein there is extracted from the receiving device a gear member which is not displayed as the extracted gear member by said gear-display device.

4. A dental treatment installation according to claim 3, including a single display device which constitutes said fault display device and a further display device provided for displaying the particular operating parameter.

5. A dental treatment installation according to claim 4, including means for cyclically and successively interrogating the tool receiving locations and/or the gear members, with respect to the presence of a tool or gear member, so that on ascertaining a deviation between the supplying conditions at one and the same receiving location, during two successive interrogations, a display signal is provided and on the occurrence of which the address designating that the appropriate receiving location is employed as the address to designate an employed tool or gear member.

6. A dental treatment installation according to claim 5, including separate display elements adjacent the receiving location for indicating the gear members required on determining a treatment instrument, a tool and the nature of cooling provided.

7. A dental treatment installation according to claim 6, in which said separate display elements comprise one of the group consisting of photodiodes and incandescent lamps.

8. A dental treatment installation according to claim 3, including a coil associated with each of said receiving locations and connected to an oscillator, the transmitted oscillation signals of which possess amplitude values which differ from each other according to the presence or absence of a tool or gear member at its respective receiving location, and the occurrence of a deviation of such a value from a reference value being employed for supplying a display signal.

9. A dental treatment installation according to claim 8, in which each of said coils comprises an air-core coil.

10. A dental treatment installation according to claim 8, in which the coils of said receiving locations are connected to follow cyclically one upon the other with said oscillator.

11. A dental treatment installation according to claim 10, including two separate stores for storing the signals corresponding, due to interrogation of in each particular instance one and the same receiving locations during two successive interrogation cycles, the signals associated in each particular instance with one and the same coil of said two separate stores being compared with each other while supplying a display signal.

12. A dental treatment installation according to claim 10, including an address generator for transmitting addresses designating all said receiving locations, and a decoder operable to derive from said addresses control signals for closing switches via which said coils are connected to said oscillator.

13. A dental treatment installation according to claim 3, including a display instrument arranged, after removal of a tool and/or transmission member from its associated receiving location, to be controlled to transmit a separate display signal, preferably a blinking signal.

14. A dental treatment installation according to claim 1, including a counter for retaining the operational data ascertained by said main control device, the particular counter position of said counter being variable by separate triggering.

15. A dental treatment installation according to claim 14, in which the counter position of said counter, or an operational data-information derived therefrom, is storable in one of said stores associated with said main control device, under the just-available operational data address (tool address and material address).

16. A dental treatment installation according to claim 1, in which there is storable in one of said stores associated with said main control device, separately, data associated with an original loading program, and which correspond to the ascertainment values upon employment of the treatment instruments and tools.

17. A dental treatment installation according to claim 1, including an instrument receiving device and first and second dental treatment instruments associated therewith, and means for displaying operational data relevant to said second treatment instrument subsequent to extraction of said second treatment instrument from said instrument receiving device after already effected extraction of said first treatment instrument upon the supply of a separate actuation signal.

18. A dental treatment installation comprising:
- at least one dental treatment instrument;
- a plurality of implements having different operating parameters for replaceable mounting in said at least one treatment instrument, said implements having variable, interchangeable operating parameters;
- a main control device operatively associated with said one dental treatment instrument and said plurality of implements;
- an implement store for storing said implements, said implement store including means to transmit to said control device variable operating parameters of the respectively employed implement upon its extraction from said implement store;
- means for transmitting to said main control device, the variable operating parameters of said at least one dental treatment instrument;
- said control device computes from the operating parameters of said at least one dental treatment instrument the operating point for the drive thereof, and computes from the variable operating parameters of said respectively employed implement and which computes therefrom the operating point for the drive of the respectively employed treatment instrument; and
- a control unit in said control device storing and automatically making available the operating data of the individual implements in said implement store responsive to the extraction of said implement from said implement store to provide the operating parameters of the respectively employed implement upon extraction which are required for computing the operating point, whereby extraction of said implement from said implement store automatically causes a specific address which provides for the connection with said control unit for providing the determining operating parameters for said implement indicated under the address in question.

* * * * *